United States Patent
Li et al.

(10) Patent No.: US 12,053,385 B2
(45) Date of Patent: Aug. 6, 2024

(54) PARTITION DESIGN AND MOLDING METHOD FOR ACETABULAR CUP PROSTHESIS WITH POROUS SURFACE

(71) Applicant: HUAZHONG UNIVERSITY OF SCIENCE AND TECHNOLOGY, Hubei (CN)

(72) Inventors: Dongdong Li, Hubei (CN); Yuanyuan Li, Hubei (CN); Dongxu Chen, Hubei (CN)

(73) Assignee: HUAZHONG UNIVERSITY OF SCIENCE AND TECHNOLOGY, Hubei (CN)

( * ) Notice: Subject to any disclaimer, the term of this patent is extended or adjusted under 35 U.S.C. 154(b) by 0 days.

(21) Appl. No.: 18/534,691

(22) Filed: Dec. 10, 2023

(65) Prior Publication Data
US 2024/0207054 A1 Jun. 27, 2024

Related U.S. Application Data

(63) Continuation of application No. PCT/CN2023/109505, filed on Jul. 27, 2023.

(30) Foreign Application Priority Data

Dec. 22, 2022 (CN) .......................... 202211655138.6

(51) Int. Cl.
*A61F 2/34* (2006.01)
*A61F 2/30* (2006.01)

(52) U.S. Cl.
CPC ............ *A61F 2/34* (2013.01); *A61F 2/30771* (2013.01); *A61F 2002/30784* (2013.01); *A61F 2002/3092* (2013.01)

(58) Field of Classification Search
CPC .......................... A61F 2/34; A61F 2002/3092
See application file for complete search history.

(56) References Cited

U.S. PATENT DOCUMENTS

2014/0363481 A1   12/2014   Pasini et al.
2015/0018956 A1   1/2015    Steinmann et al.

FOREIGN PATENT DOCUMENTS

CN   105578994    5/2016
CN   108814773    11/2018
(Continued)

OTHER PUBLICATIONS

"International Search Report (Form PCT/ISA/210) of PCT/CN2023/109505," mailed on Oct. 24, 2023, pp. 1-5.
(Continued)

*Primary Examiner* — Javier G Blanco
(74) *Attorney, Agent, or Firm* — JCIPRNET

(57) ABSTRACT

A partition design and molding method for an acetabular cup prosthesis with a porous surface includes the following: modeling of a spherical shell of an acetabular cup; cutting of the spherical shell of the acetabular cup into equal parts; integrated design on a porous layer of a surface of the partitioned acetabular cup prosthesis; reorganization of the partitioned acetabular cup prosthesis; construction of a hemispherical acetabular cup prosthesis; and 3D printing and manufacturing of the acetabular cup prosthesis. Through the disclosure, the formed porous layer is perpendicular to the surface of the acetabular cup, so favorable mechanical properties are provided. A fully interconnected branch-rod structure is provided, and there is no isolated rod, so that inflammation or even re-revision led by the detachment of isolated rods during long-term postoperative activities is prevented.

5 Claims, 4 Drawing Sheets

(56) References Cited

FOREIGN PATENT DOCUMENTS

| CN | 109009572 | | | 12/2018 | | |
|---|---|---|---|---|---|---|
| CN | 109106475 | | | 1/2019 | | |
| CN | 111297519 | | | 6/2020 | | |
| CN | 111449808 | | | 7/2020 | | |
| CN | 112404431 | A | * | 2/2021 | ......... | A61F 2/30767 |
| CN | 114601600 | | | 6/2022 | | |
| CN | 114948350 | | | 8/2022 | | |
| CN | 115462935 | | | 12/2022 | | |
| CN | 115813615 | | | 3/2023 | | |

OTHER PUBLICATIONS

"Written Opinion of the International Searching Authority (Form PCT/ISA/237) of PCT/CN2023/109505," mailed on Oct. 24, 2023, pp. 1-5.

* cited by examiner

PARTITION DESIGN AND MOLDING METHOD FOR ACETABULAR CUP PROSTHESIS WITH POROUS SURFACE

CROSS-REFERENCE TO RELATED APPLICATION

This application is a continuation of international PCT application serial no. PCT/CN2023/109505, filed on Jul. 27, 2023, which claims priority benefit of China patent application No. 202211655138.6 filed on Dec. 22, 2022. The entirety of each of the above-mentioned patent applications is hereby incorporated by reference herein and made a part of this specification.

BACKGROUND

Technical Field

The disclosure belongs to the technical field related to orthopedic medical devices, and in particular, relates to a partition design and molding method for an acetabular cup prosthesis with a porous surface.

Description of Related Art

The hip joint is the bridge between the lower limbs and the trunk of the human body. However, diseases such as femoral head necrosis, hip arthritis, and congenital hip dysplasia can seriously affect the patient's movement and even cause the patient to lose the ability to take care of him/herself. Therefore, the patient requires total hip replacement surgery to restore functions of the hip joint. At present, hip replacement has become a common surgery in medical surgery. In total hip surgery, the femoral stem and acetabular cup are key to the patient's postoperative quality of life. In particular, for acetabular cups, the conventional manufacturing process of acetabular cups is formed by casting of solid parts and surface coating. Although the surface coating improves the surface roughness of the acetabular cup, human tissue has difficulty growing into the surface coating most of the time. Therefore, during the patient's long-term activities, the all-solid acetabular cup has a greater risk of detachment, so the patient must undergo a second surgery, but the revision process causes pain and brings additional medical expenses to the patient.

In the related art, a conventional solution is to design a porous structure on the surface of the acetabular cup, and this structure can promote the ingrowth of new bone after implantation, so that the strength of the bone-implant interface can be improved and the risk of detachment is lowered. Two types of porous structure designs for the surface of the acetabular cup are mainly provided at present. One is by applying a disordered porous structure to the surface of the acetabular cup (e.g., patent "CN 108814773 A: generation method of three-dimensional model of acetabular cup bone trabecula structure and related components"). However, in fact, in the SLM manufacturing process, the forming accuracy of a large number of disordered rods is low, and even some rods with low tilt angles or hanging ones cannot be formed, so the mechanical properties are difficult to guarantee.

The other provides a regular array of porous structural unit cells on the entire hemispherical surface (e.g., patent "CN 111449808: material increase manufactured porous tantalum metal acetabulum outer cup and preparation method thereof"). However, due to the different radii of the circular arrays, many adjacent unit cells are not completely connected, resulting in a large number of isolated rods. During the patient's long-term activities after surgery, these isolated rods may be detached, and the metal particles and rods that are detached may lead to inflammation. In severe cases, the patient may require a second surgery.

Therefore, there is an urgent need for further research and improvement in the art in order to obtain a safer and more reliable acetabular cup prosthesis product.

SUMMARY

In response to the above defects or needs in the related art, the disclosure aims to provide a partition design and molding method for an acetabular cup prosthesis with a porous surface in which the entire design and the molding process are adjusted and the key steps are optimized, the presence of isolated rods or unit cells when a porous layer is designed on a surface of an acetabular cup hemisphere is effectively avoided compared to the related art, the 3D printing precision of the acetabular cup prosthesis is significantly improved, and inflammation led by rod detachment can be prevented, so that the service life of the acetabular cup prosthesis is further improved.

To achieve the above, according to the disclosure, a partition design and molding method for an acetabular cup prosthesis with a porous surface is provided, characterized in that, the method includes the following steps.

Step 1: modeling of a spherical shell of an acetabular cup

A model of the spherical shell is built, and the spherical shell corresponds to a solid part of an acetabular cup implant.

Step 2: cutting of the spherical shell of the acetabular cup into equal parts

The spherical shell is cut into equal parts by using a plurality of reference planes, and an arcuate shell cut into equal parts is obtained.

Step 3: integrated design on a porous layer of a surface of the partitioned acetabular cup prosthesis Pre-selected unit cells are arranged in an array at a specific spacing along XYZ three-axis directions of a same plane these unit cells are combined to form the corresponding porous layer, the porous layer is then attached to an outer surface of the arcuate shell cut into equal parts, and an arcuate acetabular cup prosthesis model is accordingly formed.

Step 4: reorganization of the partitioned acetabular cup prosthesis

The arcuate acetabular cup prosthesis model is mirrored along a side surface, and a spherical acetabular cup prosthesis model is accordingly reorganized and formed.

Step 5: construction of a hemispherical acetabular cup prosthesis

The spherical acetabular cup prosthesis model is then cut into two halves, edge enhancement is performed, and a hemispherical acetabular cup prosthesis model is accordingly obtained.

Step 6: 3D printing and manufacturing of the acetabular cup prosthesis

Positioning holes and fixing holes are arranged in the hemispherical acetabular cup prosthesis model, 3D printing is then performed based on the hemispherical acetabular cup prosthesis model, and a required acetabular cup prosthesis product with a porous surface is accordingly obtained.

Further preferably, in step (1), a thickness of the spherical shell is designed according to clinical needs.

Further preferably, in step (2), the process of cutting into equal parts is preferably designed as follows: 8, 32, or 128 evenly distributed points are picked on a surface of the spherical shell first, four adjacent points that can form a quadrilateral are selected, and the four points are connected to form a rectangle.

Four reference planes are established based on four sides of the rectangle and each of the points, the spherical shell is then cut with these four reference planes, and the arcuate shell cut into equal parts is accordingly obtained.

Further preferably, in step (2), the cutting into equal parts is preferably 6 equal parts, 24 equal parts, or 96 equal parts, and the arcuate shell is preferably formed by four side surfaces and two inner and outer arcuate surfaces together.

Further preferably, in step (3), the porous unit cells can be of any shape or a free combination of a plurality of types of unit cells, and the formed porous layer can be a porous layer of any complex shape.

Further preferably, in step (3), the arcuate acetabular cup prosthesis is formed by the arcuate shell cut into equal parts and the porous layer located on the outer surface of the arcuate shell together.

Further preferably, in step (5), a method of the edge enhancement is preferably designed as follows. A thickened layer is arranged on an edge of the bisected contour. A thickness of the thickened layer is equal to a sum of a thickness of an arcuate shell of the hemispherical acetabular cup prosthesis and a thickness of the porous layer.

Further preferably, in step (6), the positioning holes and the fixing holes are preferably screw holes, and the screw holes penetrate through the arcuate shell of the hemispherical acetabular cup prosthesis.

In general, the above technical solution provided by the disclosure has the following technical advantages compared to the related art.

(1) The acetabular cup prosthesis provided by the disclosure is formed by an acetabular cup body and a porous structure closely combined with the surface. Through the unique partition design on the surface of the hemispherical acetabular cup, the porous structure is first arrayed onto a flat surface and then "flows" to the partitioned hemispherical surface of the acetabular cup. In this way, the required acetabular cup prosthesis with the porous surface may be obtained in an easy-to-operate, efficient, and high-quality manner.

(2) The solution provided by the disclosure is a universal method that can address the current porous structure design on the surface of the acetabular cup, and its partition design and molding method are applicable to all porous structures. Compared to the general disordered structure or porous structure arrayed on the entire hemispherical surface, the advantage of the porous structure with partition design on the surface of the acetabular cup is that the porous structure can be any complex and any shape porous structure. Any porous structure that can be modeled on a planar basis can be well molded to the surface of the acetabular cup. Correspondingly, the existence of isolated single cells and rods is eliminated, and the risk of further inflammation led by the detachment of the porous structure caused by the patient's long-term activities after surgery is avoided.

(3) Besides, in the disclosure, the normal direction of the partition-designed porous structure unit cells is perpendicular to the surface of the acetabular cup, so favorable mechanical properties are provided. Simple and arbitrarily adjustable pore size and porosity are provided. The bone ingrowth performance can be significantly improved and the life of the acetabular cup prosthesis can be extended, which is of great significance in total hip replacement surgery.

DESCRIPTION OF THE EMBODIMENTS

In order to make the objectives, technical solutions, and advantages of the embodiments of the disclosure clearer, description will now be made in detail to clearly and completely present preferred embodiments of the disclosure, examples of which are illustrated in the accompanying drawings. Nevertheless, the disclosed embodiments are merely part of the embodiments of the disclosure, not all the embodiments. Based on the embodiments of the disclosure, all other embodiments obtained by a person having ordinary skill in the art without making any inventive effort fall within the scope that the disclosure seeks to protect.

Figure 1:
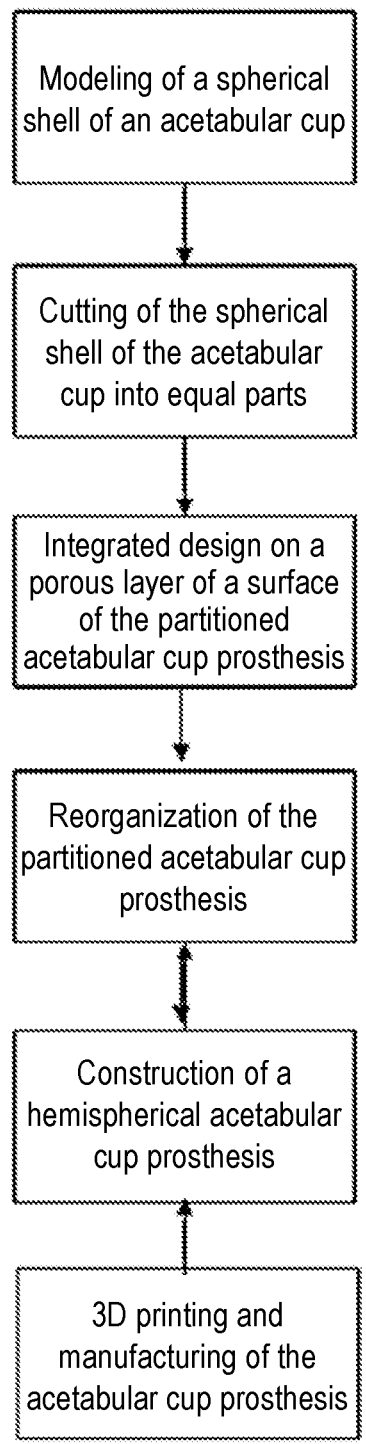
FIG. 1 is a flow chart of an overall process of a partition design and molding method for an acetabular cup prosthesis according to the disclosure.

FIG. 1 is a flow chart of an overall process of a partition design and molding method for an acetabular cup prosthesis according to the disclosure. The disclosure will be explained in more detail in the following paragraphs with reference to FIG. 1.

The first is the modeling step of a spherical shell of an acetabular cup.

In this step, a model of the spherical shell is built, and the spherical shell corresponds to a solid part of an acetabular cup implant.

Figure 2:
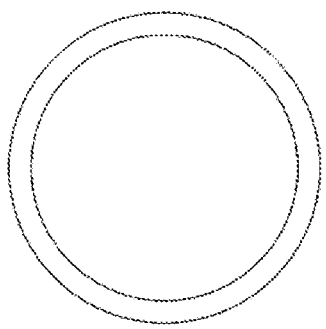
FIG. 2 is a schematic view for exemplarily illustrating a modeled spherical shell according to the disclosure.
Figure 3:
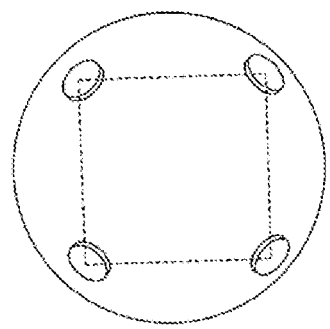
FIG. 3 is a schematic view of establishment of four reference planes on a surface of the spherical shell according to a preferred embodiment of the disclosure.
Figure 4:
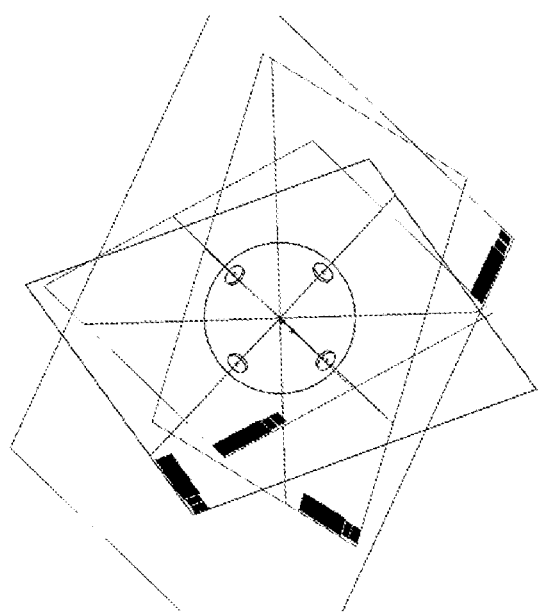
FIG. 4 is a schematic view for exemplarily illustrating the use of the reference planes to cut the spherical shell into equal parts.

To be more specific, with reference to FIG. 2, for example, three-dimensional modeling software may be used to create a spherical shell that will serve as the solid part of the acetabular cup implant.

Next is the step of cutting of the spherical shell of the acetabular cup into equal parts.

In this step, the spherical shell is cut into equal parts by using a plurality of reference planes, and an arcuate shell cut into equal parts is obtained.

Figure 5:
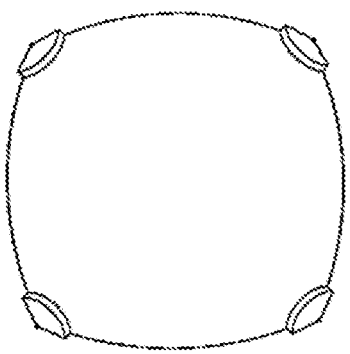
FIG. 5 is a schematic view for exemplarily illustrating an arcuate shell obtained after being cut into equal parts.
Figure 6:
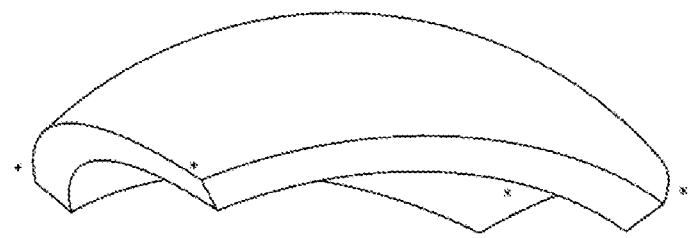
FIG. 6 is a schematic view of ⅙ of the obtained arcuate shell according to a preferred embodiment of the disclosure.

To be more specific, with reference to FIG. 3 to FIG. 6, according to a preferred embodiment of the disclosure, for instance, 8 evenly distributed points on a surface of the spherical shell may be picked, four adjacent points that can form a quadrilateral are selected, and the four points are connected to form a rectangle. Four reference planes are established based on four sides of the rectangle and the points next, and the spherical shell is cut with the four reference planes. After cutting is performed, the arcuate shell with the abovementioned positioning points cut into 6 equal parts is obtained, as shown in FIG. 5. Further, the arcuate shell cut into 6 equal parts is processed, a positioning platform is cut off, and the arcuate split into 6 parts as shown in FIG. 6 is obtained.

Next is the integrated design on a porous layer of a surface of the partitioned acetabular cup prosthesis.

In this step, pre-selected unit cells are arranged in an array at a specific spacing along XYZ three-axis directions of a same plane, these unit cells are combined to form the corresponding porous layer, the porous layer is then attached to an outer surface of the arcuate shell cut into equal parts, and an arcuate acetabular cup prosthesis model is accordingly formed.

Figure 7:
FIG. 7 is a schematic view of a selected negative Poisson's ratio unit cell according to a preferred embodiment of the disclosure.

To be more specific, as shown in FIG. 7, the unit cells may be negative Poisson's ratio unit cells, but the unit cells may also be arbitrarily complex and arbitrarily shaped porous structures. Any porous structure that can be modeled on a planar basis can be well molded to the surface of the acetabular cup. Correspondingly, the existence of isolated single cells and rods is eliminated, and the risk of further inflammation led by the detachment of the porous structure caused by the patient's long-term activities after surgery is avoided.

Next is the step of reorganization of the partitioned acetabular cup prosthesis.

Figure 8:
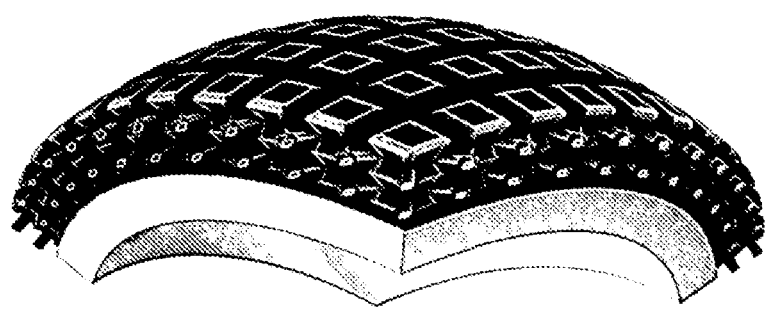
FIG. 8 is a schematic view for exemplarily illustrating an arcuate acetabular cup prosthesis formed after a porous layer is attached to a surface of the arcuate shell.

In this step, as shown in FIG. 8, the arcuate acetabular cup prosthesis model may be mirrored along a side surface, and a spherical acetabular cup prosthesis model is accordingly reorganized and formed.

Next is the construction step of a hemispherical acetabular cup prosthesis.

Figure 9:
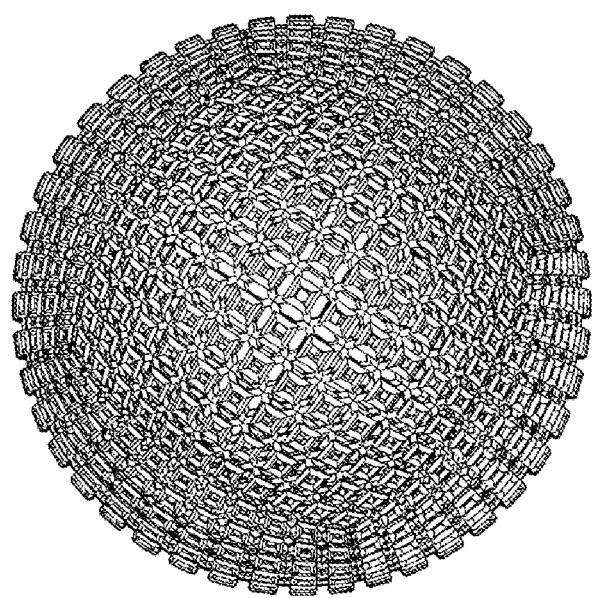
FIG. 9 is a schematic view for exemplarily illustrating a spherical acetabular cup prosthesis obtained after reorganization.

In this step, as shown in FIG. 9, the spherical acetabular cup prosthesis model may be cut into two halves, edge enhancement is performed, and a hemispherical acetabular cup prosthesis model is accordingly obtained.

Finally, it is the 3D printing and manufacturing step of the acetabular cup prosthesis.

Figure 10:
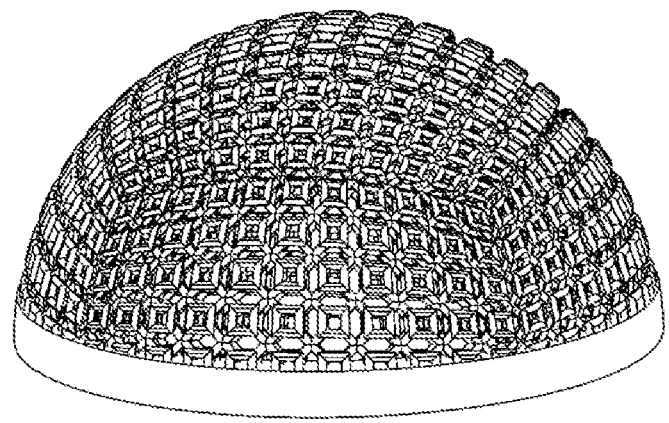
FIG. 10 is a schematic view for exemplarily illustrating a final constructed hemispherical acetabular cup prosthesis.

In this step, as shown in FIG. 10, positioning holes and fixing holes are arranged in the hemispherical acetabular cup prosthesis model, 3D printing is then performed based on the hemispherical acetabular cup prosthesis model, and a required acetabular cup prosthesis product with a porous surface is accordingly obtained.

In view of the foregoing, in the disclosure, by designing the entire preparation process and the core steps, the porous layer of the obtained acetabular cup with the porous surface is perpendicular to the surface of the acetabular cup, and favorable mechanical properties are thereby provided. A fully interconnected branch-rod structure is also provided, and there is no isolated rod, so that inflammation or even re-revision led by the detachment of isolated rods during long-term postoperative activities is prevented. In addition, the porous structure of the porous layer can be any complex and any shaped porous structure. Any porous structure that can be modeled on a planar basis can be well molded to the surface of the acetabular cup. The pore size and porosity may be designed to promote bone ingrowth, and the need for long-life and highly biocompatible acetabular cup prosthesis implant may be satisfied, so the disclosure has broad application prospects.

A person having ordinary skill in the art should be able to easily understand that the above description is only preferred embodiments of the disclosure and is not intended to limit the disclosure. Any modifications, equivalent replacements, and modifications made without departing from the spirit and principles of the disclosure should fall within the protection scope of the disclosure.

What is claimed is:

1. A partition design and molding method for an acetabular cup prosthesis with a porous surface, wherein the method comprises the following steps:
    step 1—modeling of a spherical shell of an acetabular cup:
    building a model of the spherical shell, wherein the spherical shell corresponds to a solid, non-porous part of an acetabular cup implant;
    step 2—cutting of the spherical shell of the acetabular cup into equal parts:
    cutting the spherical shell into the equal parts by using a plurality of reference planes and obtaining arcuate shells of equal size and shape after being cut into the equal parts, wherein each of the arcuate shells is formed by four side surfaces, an inner arcuate surface, and an outer arcuate surface;
    step 3—integrated design on a porous layer of a surface of a partitioned acetabular cup prosthesis:
    arranging pre-selected unit cells in an array at a specific spacing along XYZ three-axis directions of a same plane, combining these pre-selected unit cells to form a corresponding porous layer, then attaching the corresponding porous layer to an outer surface of a corresponding arcuate shell, and accordingly forming an arcuate acetabular cup prosthesis model, wherein the arcuate cup prosthesis model is formed by the arcuate shells having the porous layers on their outer surfaces;
    step 4—reorganization of the partitioned acetabular cup prosthesis:
    mirroring the arcuate acetabular cup prosthesis model along a side surface and accordingly reorganizing and forming a spherical acetabular cup prosthesis model;
    step 5—construction of a hemispherical acetabular cup prosthesis;
    then cutting the spherical acetabular cup prosthesis model into two halves, performing edge enhancement, and accordingly obtaining a hemispherical acetabular cup prosthesis model; and
    step 6-3D printing and manufacturing of the acetabular cup prosthesis;
    arranging positioning holes and fixing holes in the hemispherical acetabular cup prosthesis model, then performing 3D printing based on the hemispherical acetabular cup prosthesis model, and accordingly obtaining an acetabular cup prosthesis with the porous surface.

2. The partition design and molding method for the acetabular cup prosthesis with the porous surface according to claim 1, wherein in the step (2), the process of cutting into the equal parts is designed as follows:
    picking 8, 32, or 128 evenly distributed points on a surface of the spherical shell first, selecting four adjacent points that can form a quadrilateral, connecting the four points to form a rectangle, establishing four reference planes based on four sides of the rectangle and each of the points, then cutting the spherical shell with the four reference planes, and accordingly obtaining the arcuate shells.

3. The partition design and molding method for the acetabular cup prosthesis with the porous surface according to claim 2, wherein in the step (2), the equal parts comprise 6 equal parts, 24 equal parts, or 96 equal parts.

4. The partition design and molding method for the acetabular cup prosthesis with the porous surface according to claim 1, wherein in the step (5), the performing edge enhancement comprises: arranging a thickened layer on edges of contours of the two halves, wherein a thickness of the thickened layer is equal to a sum of a thickness of an arcuate shell of the hemispherical acetabular cup prosthesis and a thickness of the porous layer.

5. The partition design and molding method for the acetabular cup prosthesis with the porous surface according to claim 1, wherein in the step (6), the positioning holes and the fixing holes comprise screw holes, and the screw holes penetrate through an arcuate shell of the hemispherical acetabular cup prosthesis.

* * * * *